United States Patent [19]

Schulte

[11] Patent Number: 4,713,377
[45] Date of Patent: Dec. 15, 1987

[54] METHOD OF AMELIORATING OBSTRUCTIONS OF THE BOWEL

[76] Inventor: Thomas L. Schulte, 218 Family Farm Dr., Woodside, Calif. 94062

[21] Appl. No.: 936,282

[22] Filed: Dec. 1, 1986

Related U.S. Application Data

[63] Continuation-in-part of Ser. No. 697,101, Feb. 1, 1985, Pat. No. 4,626,530, which is a continuation-in-part of Ser. No. 517,417, Jan. 17, 1984, Pat. No. 4,497,824, and a continuation-in-part of Ser. No. 456,896, Jan. 10, 1983, Pat. No. 4,469,702, said Ser. No. 517,417, and Ser. No. 456,896, each is a continuation-in-part of Ser. No. 276,566, Jun. 23, 1981, Pat. No. 4,369,190.

[51] Int. Cl.$^4$ ............................................ A61K 31/615
[52] U.S. Cl. ................................................ 514/166
[58] Field of Search ...................................... 514/166

[56] References Cited

U.S. PATENT DOCUMENTS 3,551,554  8/1968  Hershler ............................. 514/166
4,073,897  2/1978  Karlor ................................ 514/166

*Primary Examiner*—Stanley J. Friedman
*Attorney, Agent, or Firm*—Millen & White

[57] ABSTRACT

Blockage of the bowel is ameliorated by the rectal administration of β-diethylaminoethyl 3-phenyl-2-hydroxybenzoate (biphenamine).

18 Claims, No Drawings

METHOD OF AMELIORATING OBSTRUCTIONS OF THE BOWEL

CROSS-REFERENCE TO RELATED APPLICATIONS

This is a continuation-in-part of application Ser. No. 697,101, now U.S. Pat. No. 4,626,530, which was filed Feb. 1, 1985 as a continuation-in-part of application Ser. No. 517,417, filed Jan. 17, 1984, now U.S. Pat. No. 4,497,824, and of Ser. No. 456,896, filed Jan. 10, 1983, now U.S. Pat. No. 4,469,702, both filed as a continuation-in-part of application Ser. No. 276,566, filed June 23, 1981, now U.S. Pat. No. 4,369,190.

BACKGROUND OF THE INVENTION

This invention relates to a method of ameliorating obstructions of the bowel.

The compositions of this invention comprise biphenamine ($\beta$-diethylaminoethyl 3-phenyl-2-hydroxybenzoate) base or pharmaceutically acceptable acid addition salt thereof. Salts of this compound are known to have a variety of activities, including local anesthetic (U.S. Pat. No. 1,976,922); treatment of seborrhea capitis in a shampoo (U.S. Pat. No. 3,123,531); as well as antihistaminic and bactericidal activity and fungicidal properties (U.S. Pat. No. 2,594,350; Report Annual Meeting So. Med. Assoc., Nov. 6, 1961).

Biphenamine hydrochloride has been sold as a 1% ointment, under the trademark "Melsaphine," as a topical anesthetic agent possessing bactericidal, fungicidal and antihistamine properties and as a 1% aqueous shampoo under the trademark "Alvinine," Federal Register, Vol. 34, No. 189, page 153, Oct. 2, 1969. See also U.S. Pat. No. 3,123,531.

Although its use in a shampoo for treating seborrhea and related conditions is claimed in U.S. Pat. No. 3,123,531, nothing was known concerning its ability to ameliorate blockage of the bowel by the rectal administration thereof.

My prior U.S. Pat. No. 4,626,530 relates to the use of biphenamine for the treatment of eye inflammation, my U.S. Pat. No. 4,497,824 relates to the use of biphenamine as a non-toxic, nonallergenic bacteriostat and fungistat which is also effective in promoting the normal healing of traumatized or pathological epithelium by suppressing infection and/or the natural inflammatory process, and my U.S. Pat. Nos. 4,369,190 and 4,469,702 relate to analgesic biphenamine compositions and their use to ameliorate intractable pains.

I have now found that the rectal administration of biphenamine is effective in ameliorating a variety of genital and colonary abnormalities and is especially effective in ameliorating abnormal states which result in the partial or complete blockage of the bowel, either by ameliorating the swelling and inflammation associated with the abnormal state or by improving or curing the abnormal state itself, or both.

SUMMARY OF THE INVENTION

According to a primary aspect of this invention, an obstruction of the bowel is ameliorated by the rectal administration to the affected patient of an amount of biphenamine effective to enlarge the fecal passage of the bowel proximate the source of the obstruction.

According to other aspects of the invention, other abnormal states, such as urinary bladder and vaginal infections, are ameliorated by the rectal administration of biphenamine.

The term "ameliorate" as used herein means the obstruction is diminished or eliminated, usually by shrinking the size of the cause or source of the obstruction. The term "obstruction" means a pathological condition of the bowel or tissue proximate thereto which partially or totally blocks the normal pathway for feces in the colon. Such obstructions include hemorrhoids, both internal and external, bowel spasms associated with diverticulitis and solid tumors, both benign, e.g., polyps, and cancerous, e.g., carcinomas, of the bowel and anus, as well as cancers proximate the bowel, e.g., metasthesized carcinoma of the prostate and liver. Although conclusive clinical evidence that the progression of the cancerous condition is reversed has not yet been obtained, objective and subjective improvement in the blockage of the colon associated with tumors of the colon and anus has been observed repeatedly clinically. However, this could be due to a reduction in the inflammation and swelling associated with the pathological condition.

DETAILED DISCUSSION

The biphenamine (base or acid addition salt thereof) is administered rectally, ordinarily as a mixture in a pharmaceutically acceptable carrier or diluent, preferably aqueous. The mixture preferably is liquid, e.g., in the form of a clear solution or spray, or in the form of a lotion or other viscous aqueous liquid. The mixture can also be semi-solid or solid, e.g., in the form of an ointment, cream or suppository. Viscosity regulating agents, such as thickeners and gelling agents, e.g., glycerin, sodium carboxymethyl-cellulose, etc., can also be used to regulate flowability. See U.S. Pat. Nos. 3,740,420 and 3,711,602, whose disclosures are incorporated herein by reference. The biphenamine and carrier therefor can be in the form of an oil-in-water or water-in-oil emulsion, as disclosed in U.S. Pat. No. 3,740,420, or as a single phase aqueous solution, the latter being preferred. Organic solvents, e.g., ethanol, can also be present.

Although the biphenamine present in the mixture can be employed at any convenient concentration, generally concentrations of up to 1% by weight, e.g., from about 0.001 to 1%, preferably about 005 to 0.5% are employed. It preferably is present in the form of a pharmaceutically acceptable salt thereof, e.g., hydrochloride, hydrobromide, sulfate, phosphate, acetate, succinate, tartrate, benzoate, citrate, lactate or maleate, preferably the hydrochloride. Although acid addition salts of biphenamine are disclosed in U.S. Pat. No. 1,976,922 as having local anesthetic activity at a 2% concentration, neither its ability to ameliorate blockage of the bowel or for any other purpose when administered rectally at lower concentrations is not suggested.

The biphenamine is administered rectally on successive occasions, e.g., as frequently as every hour or as infrequently as once daily or longer, depending on the severity and intractability of the pathological condition. Generally, administration at least once every 24 hours for 2-30 days or longer is preferred.

The amount of the biphenamine administered will depend on such factors as the cause of the blockage, the concentration of biphenamine in the mixture administered and the individual's responsiveness to the therapy. Usually, about 5 to 100 mg. per dose, preferably about 5 to 20 mg. per dose, is administered. The effectiveness of successively greater or smaller dosages can determine the optimum effective individual dose. The mixture can be administered with a needleless hypodermic, eye dropper, or a collapsible plastic bottle with a cap fitted with a rectal tip dispenser, or in the form of a suppository.

The compositions of this invention are also effective for the amelioration of the pain associated with the condition being treated. When a composition of this invention is administered on successive occasions, not only is pain promptly ameliorated or eliminated, the healing process is facilitated, apparently by the suppression of the inflammatory response and infection. The compositions of this invention are useful for promoting the healing of a variety of pathological conditions of the bowel and topically accessible areas of the body, e.g., those caused by viral, bacterial, fungal and other microorganism infections or by localized inflammatory conditions, particularly those which produce a lesion in the bowel or a pathological growth therein, such as benign or tumorous tissue, e.g., herpes virus lesions and fungus infections of the urinary bladder, urethra and vagina.

Although biphenamine hydrochloride as a 1% ointment is known to be useful for the treatment of minor burns, minor skin irritations or insect bites and to have bactericidal, fungicidal and antihistaminic properties at that concentration, it is surprising that concentrations thereof of only about 0.1% are effective when administered rectally. Although U.S. Pat. No. 2,594,350 teaches that a 0.14% solution of the mandelic acid salt of biphenamine is useful as a urinary antiseptic and germicide, the activity thereof is due in part to the known urinary bactericidal activity of mandelic acid.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the preceding text and the following examples, all temperatures are set forth uncorrected in degrees Celsius and all parts and percentages are by weight unless otherwise indicated.

EXAMPLE 1

A 68 year old man (J. S.) with known diverticulitis diagnosed by barium enema and colonoscopy had recurrent bouts of abdominal pain with blood in the stool and alternating constipation, cramping and diarrhea. He tried diet management and medication of various types to no avail. It was suggested on several occasions that he might need surgical treatment.

Biphenamine HCl (0.1% in 15 cc distilled water) was instilled rectally once daily at bedtime. After about 7-10 days he felt more comfortable. He continued the management daily and has had no pain, constipation or other symptoms and continues to treat himself daily, because of fear of return of his prior condition.

EXAMPLE 2

A 56 year old man (S. C.) with diverticulitis and recurrent bleeding hemorrhoids had two operations for hemorrhoids. The rectal or anal bleeding recurred. He also had abdominal cramping and pain.

He instilled 15 cc biphenamine HCl 0.1% in distilled water rectally every night before bedtime. After two days he had no more bleeding. He continued instilling the biphenamine HCL 0.1% in distilled water for the next 8 months. He has had no further trouble with pain or bleeding.

EXAMPLE 3

A 75 year old woman (C. S.) with diverticuli of the colon had repeated attacks of pain and at times fever requiring antibacterial therapy. Also, at times there was a localized peritonitis requiring a very hot water bottle applied to the abdominal area for relief of pain as a counterirritant. There were also bouts of diarrhea.

Biphenamine HCl (0.1% in 15 cc distilled water) was instilled rectally every night. After one week there was a definite relief of symptoms and relief from constipation. Subsequent varium enema and colonoscopy demonstrated a reduction in the number and size of the diverticuli. She continues treatment every night because she is afraid that the symptoms will come back.

EXAMPLE 4

An 80 year old man (T. M.) with a long history of diverticuli of the colon, proven by barium enema and colonoscopy. At one time he had a severe hemorrhage that was thought to be carcinoma of the bowel. However it was determined to be due to diverticulitis. Transfusions were required. This man had about as severe a case of recurrent diverticulitis as possible, with all the complications.

He started rectal instillations of biphenamine HCl 0.1% in distilled water every night at bedtime. Within one week his symptoms were improved. He continued management with the instillations without interruption. Also he was more liberal with his diet that always previously had been very restricted. He is a very happy and pleased individual and is continuing his management. He does not want to stop treatment.

EXAMPLE 5

A 58 year old woman (F. B.) with chronic recurring diverticulitis had recurring urinary tract infections which failed to respond to treatment, both systemic and local. She was miserable with attacks of fever not only from the diverticulitis but also from the urinary tract infections.

She was started on biphenamine HCl 0.1% solution in distilled water 15 cc rectally once daily. Within one week she felt better. Also she has never had a recurrence of the urinary bladder infections since she started using the biphenamine solution.

EXAMPLE 6

A 50 year old woman (Y. N.) with cancer of the left breast and metastasis to the liver was given biphenamine HCl (0.1% solution in distilled water) 6 cc rectally twice daily. Eleven months after she was first seen, there was a definite reduction in the size of the metastasis in the liver by X-ray.

EXAMPLE 7

A 65 year old man (S. S.) with cancer of the colon and also cancer of the anus had a mass as large as a football in the buttocks. He had ribbon stools and cramping with constipation. He instilled 6 cc of the biphenamine HCl (0.1% solution in the distilled water) rectally twice daily. He returned in 6 months. The football size mass was gone and the buttocks had a normal contour. He still had ribbon stools but this was due to the fibrosis and the obvious residual cancer in the anus.

It was thought best not to operate on him at this time. He is continuing the management with the biphenamine.

EXAMPLE 8

A 71 year old man (F. D.) with carcinoma of the anus had extension into the buttocks with an indurated appearing carcinoma in both buttocks. He also had a cancer of the colon and liver by metastasis. Biphenamine HCl solution (0.1% in 15 cc distilled water) was instilled rectally once each day. After a 6 months period, there was a definite improvement in his symptoms. He was relieved of the pressure in the anal region. The extension of the tumor in the buttocks had regressed. The management is continuing.

EXAMPLE 9

A 70 year old woman (H. R.) with cancer of the breast and metastasis to the liver demonstrated by X-ray treated herself with biphenamine HCl 0.1% in distilled water, 6 cc rectally twice a day. After 6 months, there was a definite diminution in the size of the liver metastasis.

Although there is no proof thus far that the malignant disease of these patients had been cured, symptomatic improvement was observed and there has also been an objective reduction in metastasis in some cases. Some of these patients who would have been expected to succumb to their disease much earlier are still alive and the course of their disease is still being followed.

EXAMPLE 10 A 39 year old man (R. C.) with carcinoma of the anus was first seen Dec. 5, 1985. His alkaline phosphatase was 348 (normal 5–35), LDH was 552 (normal 90–200), SGOT was 79 (normal 10–50), SGPT was 79 (normal below 40). In Apr. 1986 CEA (carcinoma embryonic antigen) was 2.5-½ and alkaline phosphatase was 17.7.

During this period, biphenamine HCl 0.1% in distilled water was administered rectally 6 cc twice a day. When he returned for a follow up, there was almost a complete disappearance of the anal cancer and he also showed a diminution in the size of the metastasis in the liver as compared to the prior examination. He continued the biphenamine management an additional two months, at which time his local doctor decided, since the tumor had reduced in size to a considerable extent, it was now possible to give him the benefit of surgical treatment and a colostomy was performed.

What is claimed is:

1. A method of ameliorating an obstruction of the bowel, which comprises the rectal administration to the affected patient of an amount of biphenamine effective to enlarge the fecal passage of the bowel proximate the source of the obstruction.

2. The method according to claim 1, wherein the patient is a human being.

3. The method according to claim 1, wherein biphenamine is administered as a pharmaceutically acceptable salt thereof.

4. The method according to claim 3, wherein the salt is the hydrochloride.

5. The method according to claim 1, wherein biphenamine is administered by instillation of an aqueous solution thereof.

6. The method according to claim 1, wherein concentration of biphenamine in the solution is about 0.1%.

7. The method according to claim 1, wherein the amount of biphenamine which is administered is about 5 to 100 mg. per dose.

8. The method according to claim 1, wherein the amount of biphenamine which is administered is about 5 to 20 mg. per dose.

9. The method according to claim 1, wherein the biphenamine is administered at least once a day for a plurality of successive days.

10. The method according to claim 1, wherein the obstruction is hemorrhoidal.

11. The method according to claim 1, wherein the obstruction is a carcinoma of the bowel or anus.

12. The method according to claim 1, wherein the obstruction is a spasm of the bowel associated with diverticulitis.

13. The method according to claim 1, wherein the patient is a human being, and wherein the biphenamine is administered at least once a day for a plurality of successive days.

14. The method according to claim 13, wherein the amount of biphenamine which is administered is about 5 to 100 mg. per dose.

15. The method according to claim 14, wherein the concentration of biphenamine in the solution is about 0.1%.

16. The method according to claim 13, wherein the salt is the hydrochloride and wherein the amount of biphenamine which is administered is about 5 to 20 mg. per dose.

17. The method according to claim 16, wherein the obstruction is hemorrhoidal.

18. The method according to claim 16, wherein the obstruction is a spasm of the bowel associated with diverticulitis.

* * * * *